United States Patent [19]

Fedi et al.

[11] Patent Number: 4,931,437
[45] Date of Patent: Jun. 5, 1990

[54] 8-AZAXANTHINE DERIVATIVES, AND PHARMACEUTICAL COMPOSITIONS CONTAINING THEM

[75] Inventors: Mauro Fedi, Sesto Fiorentino; Carla Bacciarelli, Firenze; Graziano Bonacchi, Pistoia, all of Italy

[73] Assignee: Malesci Istituto Farmacobiologico S.p.A., Firenze, Italy

[21] Appl. No.: 236,219

[22] Filed: Aug. 25, 1988

Related U.S. Application Data

[63] Continuation-in-part of Ser. No. 133,391, Dec. 15, 1987, abandoned.

[30] Foreign Application Priority Data

Dec. 16, 1986 [IT] Italy .............................. 48749 A/86

[51] Int. Cl.$^5$ .................. A61K 31/505; C07D 471/02
[52] U.S. Cl. ............................ 514/234.2; 514/258; 544/118; 544/254
[58] Field of Search ............... 544/254, 118; 514/258, 514/234.2

[56] References Cited

U.S. PATENT DOCUMENTS

| | | | |
|---|---|---|---|
| 2,543,333 | 2/1951 | Parker | 544/254 |
| 4,027,025 | 5/1977 | Schaeffer | 544/254 |
| 4,146,500 | 3/1979 | Fletcher | 544/254 |
| 4,543,255 | 9/1985 | Shealy | 544/254 |
| 4,714,701 | 12/1987 | Beauchamp | 544/254 |
| 4,840,949 | 6/1989 | Korbonits et al. | 544/118 |

FOREIGN PATENT DOCUMENTS

| | | | |
|---|---|---|---|
| 0272226 | 6/1988 | European Pat. Off. | 544/254 |
| 2554027 | 10/1976 | Fed. Rep. of Germany | 544/254 |
| 0598900 | 3/1978 | U.S.S.R. | 544/254 |

OTHER PUBLICATIONS

Bariana Jour. Med. Chem. 14, 543–45 (1971).
Broughton et al., Jour. Med. Chem. 18 1117–22 (1975).
Coulson et al., Eur. Jour. Med. Chem. 9 pp. 313–317 (1974).

*Primary Examiner*—Donald G. Daus
*Attorney, Agent, or Firm*—Beveridge, DeGrandi & Weilacher

[57] ABSTRACT

The present invention relates to 8-azaxanthines derivatives having antiasthmatic activity and the general formula:

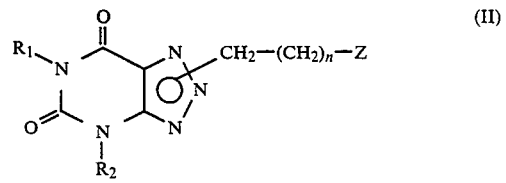

wherein:
$R_1$ is a hydrogen or a lower alkyl of from one to six carbon atoms or an arylalkyl group;
$R_2$ is a lower alkyl of from one to six carbon atoms or an aryl or an arylalkyl group;
n = from 1 to 3

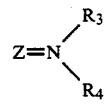

wherein:
$R_3$ and $R_4$ are lower alkyl of one to four carbon atoms or complete together a five or six member heterocycle;

and wherein the substitution in the triazole ring concerns the 7- or 8- or 9- positions: their salts which are physiologically acceptable, their pharmaceutical compositions and the process for preparing them.

14 Claims, No Drawings

8-AZAXANTHINE DERIVATIVES, AND PHARMACEUTICAL COMPOSITIONS CONTAINING THEM

This application is a continuation-in-part of a copending application Ser. No. 07/133,391 filed Dec. 15, 1987, now abandoned.

DISCLOSURE OF THE INVENTION

The present invention relates to 8-Azaxanthine derivatives, therapeutically acceptable salts thereof, processes for their preparation, and pharmaceutical compositions containing them.

In particular the present invention relates to 8-azaxanthines (I)

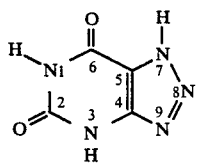

which are variously substituted in position 3 or 1 and 3 and substituted on triazole ring, as well as to the physiologically acceptable salts thereof.

Moreover, the present invention also includes the process for the preparation of the compounds, as well as some intermediate compounds for the synthesis thereof, the pharmaceutical compositions containing them and the therapeutic use of such compositions as antiasthmatic agents.

It is already known that substituted xanthines are active as bronchodilators, and indeed theophylline (1.3-dimethylxanthine) has been successfully employed for some decades in the treatment of bronchial asthma, but no therapeutically application of 8-azaxanthine derivatives exists at present.

In the literature, some azaxanthines have shown both antiallergic (Coulson C. J.; et al.—Eur. J. Med. Chem. 9, 313–317; 1974 and Broughton B. J. et al.—J. Med. Chem. 18, 1117–1122; 1975) and cardiovascular properties (Bariana D. S.—J. Med. Chem. 14, 543–545; 1971).

Moreover, it is well known that substituted xanthines and in particular theophylline, which are widely employed in the treatment of bronchial asthma, are not free for undesired side effects e.g. CNS-stimulating effects, tachycardia and hypotension.

The main object of the present invention is providing pharmacological compounds having antiasthmatic activity higher than that shown by the traditional xanthine derivatives, with a remarkable reduction of the occurrence of the above mentioned side effects on the nervous system and on the cardiovascular system.

According to the present invention, it has been found out that the introduction of dialkylaminoalkyl or heterocyclylalkyl substituents in the triazole ring of the 8-azaxanthines gives the 8-azaxanthine structure some interesting and unexpectable antiasthmatic properties with reduced circulatory and central effects.

Accordingly, the specific object of the present invention consists in the 8-azaxanthine derivatives of the general formula (II).

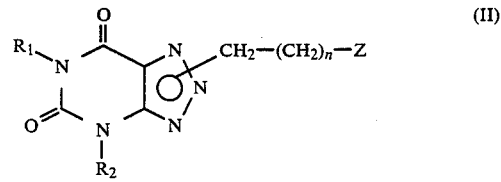

wherein:
$R_1$ is a hydrogen or a lower alkyl of from one to six carbon atoms or an arylalkyl group;
$R_2$ is a lower alkyl of from one to six carbon atoms or an aryl or an arylalkyl group;
$n$ = from 1 to 3

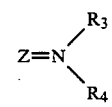

wherein:
$R_3$ and $R_4$ are lower alkyl of one to four carbon atoms or complete together a five or six member heterocycle;
and wherein the substitution in the triazole ring concerns the 7- or 8- or 9- positions. According to the present invention it has been discovered out that the products listed in tables 1a, 1b and 1c, exhibit, in some cases, an antiasthmatic activity higher than theophylline and, in addition, they do not elicit CNS stimulating and/or tachycardic effect.

TABLE 1a

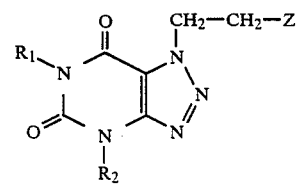

| Compound | $R_1$ | $R_2$ | Z | m.p. °C. |
|---|---|---|---|---|
| MX8280 | CH₃ | CH₃ | —N—(CH₃)₂ | oil |
| MX8277 | CH₃ | CH₃ | —N—(C₂H₅)₂ | oil |
| MX8271 | n-C₃H₇ | 2-methyl-butyl | —N—(CH₃)₂ | oil |
| MX8273 | n-C₃H₇ | 2-methyl-butyl | —N—(C₂H₅)₂ | oil |
| MX82108 | H | 2-methyl-butyl | —N—(C₂H₅)₂ | 98–100 |
| MX8294 | n-C₃H₇ | Phenyl | —N—(CH₃)₂ | 89–91 |
| MX8257 | n-C₃H₇ | Phenyl | —N—(C₂H₅)₂ | 50–53 |
| MX82103 | n-C₃H₇ | Phenyl | Piperidino | 50–52 |
| MX82105 | n-C₃H₇ | Phenyl | Morpholino | 98 |

TABLE 1b

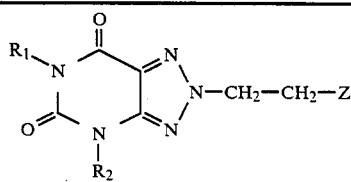

| Compound | $R_1$ | $R_2$ | Z | m.p. °C. |
|---|---|---|---|---|
| MX8283 | CH₃ | CH₃ | —N—(CH₃)₂ | 75–77 |
| MX8279 | CH₃ | CH₃ | —N—(C₂H₅)₂ | oil |
| MX8272 | n-C₃H₇ | 2-methyl-butyl | —N—(CH₃)₂ | oil |
| MX8274 | n-C₃H₇ | 2-methyl-butyl | —N—(C₂H₅)₂ | oil |
| MX82109 | H | 2-methyl-butyl | —N—(C₂H₅)₂ | 90 |
| MX8293 | n-C₃H₇ | Phenyl | —N—(CH₃)₂ | 89–91 |
| MX8258 | n-C₃H₇ | Phenyl | —N—(C₂H₅)₂ | oil |

TABLE 1b-continued

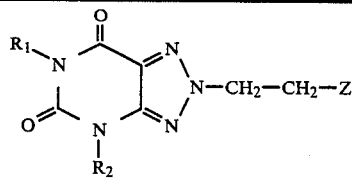

and their toxicities, as well as their side-effects, are shown in table 2.

Some of these compounds present an increase in the antibronchospastic activity up to about three times that of theophylline.

TABLE 2

| Compound | DL/50 mmoles/Kg (mouse os) | Oral antibronchospastic activity (areosol ovalbumin guinea-pig) A.U.C. O → 3h Index | Tachycardic effects (rat os) Index | Effects on CNS (mouse os) Cardiazole | Chlordiazepoxide |
|---|---|---|---|---|---|
| THEOPHYLLINE | 1,28(1,15 1,41) | 1 | 1 | ↑↑ | ↓↓ |
| MX8257 | >1,35 | 1,8 | 0 | 0 | ↑ |
| MX8258 | >1,35 | 1,6 | 0 | 0 | 0 |
| MX8271 | >1,48 | 1,9 | 0 | ↑ | ↑ |
| MX8272 | 1,37(1,16 1,61) | 2,1 | 0 | 0 | ↑ |
| MX82103 | 0,91(0,68 1,23) | 1,7 | 0 | 0 | ↑ |
| MX82104 | 1,31 | 2,1 | 0 | 0 | ↑ |
| MX82105 | >1,3 | 2,4 | 0 | 0 | ↑ |
| MX82106 | >1,3 | 2,9 | 0 | 0 | ↑ |
| MX82108 | >1,55 | 1,3 | 0 | 0 | 0 |
| MX82109 | >1,55 | 1,1 | 0,3 | 0 | 0 |

| Compound | R$_1$ | R$_2$ | Z | m.p. °C. |
|---|---|---|---|---|
| MX82104 | n-C$_3$H$_7$ | Phenyl | Piperidino | 74 |
| MX82106 | n-C$_3$H$_7$ | Phenyl | Morpholino | 122 |

TABLE 1c

| Compound | R$_1$ | R$_2$ | Z | m.p. °C. |
|---|---|---|---|---|
| MX8259 | n-C$_3$H$_7$ | Phenyl | —N—(C$_2$H$_5$)$_2$ | 101–105 |
| MX82110 | n-C$_3$H$_7$ | Phenyl | Morpholino | 135–138 |

Furthermore another advantage of these compounds is their low toxicity.

In order to demonstrate the improved activity of the compounds of this invention, the pharmacological results related to both their antibronchospastic activities The physiologically acceptable salts of the above mentioned 8-Azaxanthine derivatives are further object of the present invention.

Moreover, the pharmaceutical compositions containing above reported 8-azaxanthine derivatives or the physiologically acceptable salts thereof are also included in the scope of the present invention. Such compositions are appropriately formulated as tablets, vials, syrups, drops, aerosol, suppositories, ointments, gels, as retard forms, and so on.

Oral preparations can contain also diluting, lubricating, binding, disintegrating, colouring, flavouring, surface-active, preserving, buffering and similar agents. In the process for the preparation of the compounds of this invention (Formula II), substituted ureas were converted into substituted cyanoacetylureas by reaction with cyanoacetic acid and next cyclized to form 1 or 1,3-substituted-6-amino-2,4-(1H, 3H)-pyrimidinediones, which were converted into 5-nitroso derivatives by treating with sodium nitrite in glacial acetic acid.

1 or 1,3 substituted-5-nitroso-6-amino-2,4-(1H, 3H)-pyrimidinediones were then reduced to diamino-derivatives with sodium dithionite.

1 or 1,3-substituted-6,7-diamino-2,4-(1H, 3H)-pyrimidinediones (Scheme I) were cyclized to form 1 or 1,3-substituted azaxanthines by reacting with sodium nitrite in hydrochloric acid and next condensed with 2-dialkylaminoalkyl-chlorides or heterocyclylalkyl-chlorides.

SCHEME I

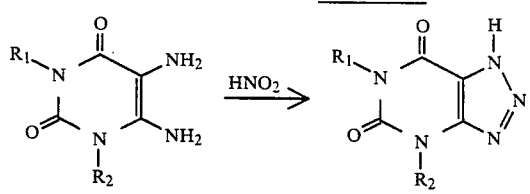

SCHEME I

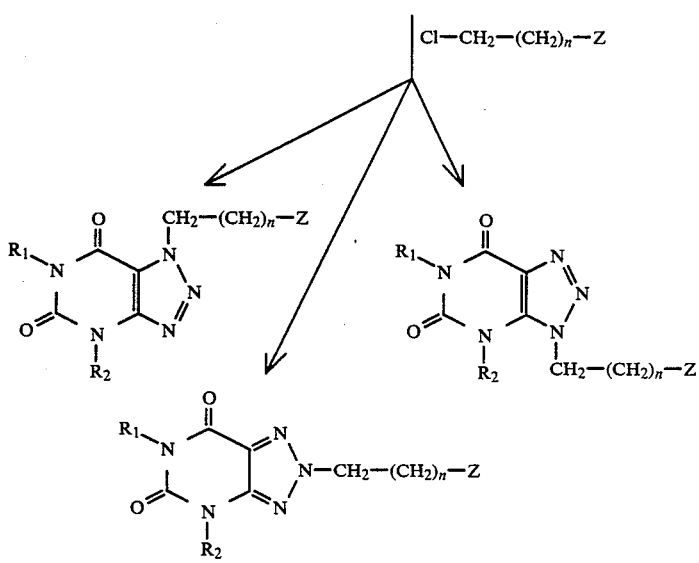

Preferably, the condensation reaction was carried out in dimethylformamide by previous treatment of azaxanthine with sodium hydride or with sodium hydroxide or by addition of potassium carbonate to the chloroformic solution of the reagents.

The mixture of obtained 7- or 8- or 9-substituted-8-azaxanthine was finally separated by fractional distillation or crystallization or by chromatographic procedures.

The structure assignment was performed by UV, NMR and X-ray studies as well as, in the case of 7-substituted azaxanthines, by direct comparison to the compounds obtained as illustrated in Scheme 2.

SCHEME 2

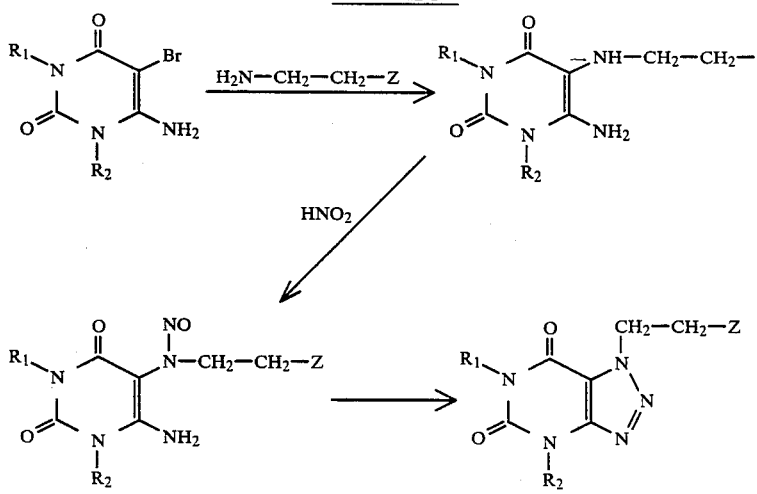

Also some 8-azaxanthines of formula (I) are included in the scope of the invention, being useful as intermediates in the preparation of derivatives of formula (II), and reported in the following table 3.

TABLE 3

| Compound | $R_1$ | $R_2$ | m.p. °C. |
|---|---|---|---|
| MX42 | n-$C_3H_7$ | 2-methyl-butyl | 109–111° |

TABLE 3-continued

| Compound | $R_1$ | $R_2$ | m.p. °C. |
|---|---|---|---|
| MX50 | H | 2-methyl-butyl | 200–202° |
| MX14 | n-$C_3H_7$ | phenyl | 171–173° |

The following examples illustrate the invention:

EXAMPLE I 1-n-propyl-3-phenyl-7-(2-morpholinoethyl)-8-azaxanthine (a) 6-amino-5-nitroso-1-phenyl-3-n-propyl-2,4-(1H,3H)-pyrimidinedione 31 g (0.36M) of cyanoacetic acid were added to a solution of 64 g (0.36M) of N-1-n-propyl-N-2-phenylurea in 200 ml of acetic anhydride. The temperature was kept at 60°–70° C. for 2 hrs.

The dry residue obtained by distillation of acetic anhydride was dissolved in 90% ethyl alcohol. The pH value was adjusted to pH 9–10 with NaOH. The solution was heated to the boiling point, cooled and evaporated to dryness. To the crystalline residue dissolved in warm 20% acetic acid were added 30 g NaNo2. After cooling, crystals were filtered off and washed twice with ethyl alcohol and ethyl ether.

Yield 50 g; m.p. 220° C.

(b) 5,6-diamino-1-phenyl-3-n-propyl-2,4-(1H, 3H)-pyrimidinedione 100 g. of Na2S2O4 were added portionwise at 80° C. to the suspension of 50 g (0.18M) of the nitroso-derivative in 400 ml 30% NH4OH.

The mixture was heated for 1 hour and, after cooling, the obtained precipitate was filtered.

Yield 26 g; m.p. 171°–173° C.

(c) 1-n-propyl-3-phenyl-8-azaxanthine

To the refluxed solution of 26 g (0.1M) of 5,6-diamino-1-phenyl-3-n-propyl-2,4-(1H, 3H)-pyrimidinedione in 10% HCl, were added portionwise 15 g of NaNo2. After cooling, crystals were filtered and recrystallized from benzene.

Yield 20 g.; m.p. 174° C.

(d) Preparation of 1-n-propyl-3-phenyl-7-(2-morpholinoethyl)-8-azaxanthine

To a mixture of 14 g of potassium carbonate and 27 g (0.1M) of 8-azaxanthine in 400 ml of chloroform was added a solution of 15 g (0.1M) of 2-morpholinoethyl chloride in 40 ml CHCl3. The mixture was stirred and refluxed for six hours, cooled to room temperature and washed with 100 ml 5% NaOH.

The organic layer was separated and the solvent was evaporated to yield 38 g of a yellow oil, which showed three spots at thin layer chromatography (t.l.c.). (Silica gel; hexane; ethylalcohol 3:3:1).

By means of preparative HPLC the three 7- or 8- or 9-substituted isomers were separated.

10 g of 7-substituted isomer (highest Rf value) were obtained. m.p. 97°–98° C. 1H-NMR (CDCl3): 5H 7,35s; 2H 4,7t; 2H 3,95t; 4H 3,5t; 2H 2,8t; 4H 2,45t; 2H 1,65m; 3H 0,95t;

EXAMPLE II 1-n-propyl-3-phenyl-8-(2-morpholinoethyl)-8-azaxanthine

The compound (intermediate Rf value) was prepared as described in Example I. m.p. 120°–122° C. 1H-NMR (CDCl3): 5H 7,35s; 2H 4,45t; 2H 3,95t; 4H 3,55t; 2H 2,85t; 4H 2,4t; 2H 1,65m; 3H 0,95t

EXAMPLE III 1-n-propyl-3-phenyl-9-(2-morpholinoethyl)-8-azaxanthine

The compound (lowest Rf value) was prepared as described in Example I. m.p. 135°–138° C. 1H-NMR (CDCl3): 5H 7,5s; 4H 3,8m; 4H 3,5t; 2H 2,4t; 4H 2,15t; 2H 1,7m; 3H 0,95t

PHARMACOLOGICAL DATA

Acute toxicity

Fasted (18 h) male Swiss mice (20 g b.w.) received orally the compounds (0.2 ml/10 g b.w.) Number of deaths, in the ten days following drug administration, was recorded. LD50 was calculated according to Litchfield and Wilcoxon method (J. Pharm. Expt. Ther. 96, 99; 1949). The maximum dose administered was generally 500 mg/Kg.

ANTIBRONCHOSPASTIC ACTIVITY

Fasted (16 h) male and female guinea pigs were sensitized by ovalbumin (25 mg/Kg. s.c. and 25 mg/Kg. i.p.) (Herxheimer and Stresemann—Arch. It. Pharmacodyn. Ther. 125.126; 1960). After two weeks, animals were challenged, by an aerosol of 0.5% ovalbumin recording the latency time ($T_1$) of the first bronchospasm. A week later, the test was repeated in the same animals 1–3 hours after drug administration ($T_2$). % of inhibition was determined as $$\left(1 - \frac{T_1}{T_2}\right) \times 100$$

where $T_1$ was control latency time, $T_2$ was latency time after drug administration. All animals exposed to the aerosol for 5' without bronchospasm were arbitrarily considered fully protected. The area under curve (AUC) expressing the % inhibition plotted toward time (0–3 h) after drug dosing, was calculated. Theophylline caused a dose-dependent inhibition of bronchoconstriction ($ED_{50}=0.25$ mmole/Kg.). The compounds were administered at a dosage similar or less than 1/5 $LD_{50}$ value and their AUCs were determined. The activity index (A.I.) was given as the ratio between equieffective doses of theophylline and tested compounds. A.I. are reported in table 2.

CARDIOVASCULAR EFFECTS

Fasted (16 h) normotensive male Wistar rats weighing 300–380 g. were used. The animals were prewarmed by means of infrared lamp for 15 min. before recording blood pressure and heart rate with the tale-cuff method (Maffii G. e Coll.—Arch. It. Sci. Farm. 12, 3; 1962). Recording were performed before and 30'-90'—3 h after oral drug administration. Theophylline caused a slight hypotension and a marked dose-dependent tachycardia. The % increase in heart rate was plotted against the log dose. Theophylline dosage producing a 30% increase in heart rate were 0.21—0.36—0.57 mmole/Kg. at 30'—90'—3 h respectively. The tachycardic indexes (calculated at 30'—90'—3 h) were evaluated as the ratio between equiactive dose of theophylline and tested compounds. In table 2 the average value of the indexes was reported.

EFFECTS ON CENTRAL NERVOUS SYSTEM

Fasted (20 h) male Swiss mice (20 g b.w.) received orally the compounds 1 h before cardiazole (CZ) or chlordiazepoxide (CDO) administration.

1-CZ INDUCED CONVULSIONS

CZ was injected i.p. in a fully convulsive dose which produced death in about 10% of animals (60–100 mg/Kg.). Appropriate dose was determined before each experimental session. Mice were observed for 1 h after CZ administration. Theophylline produced a significant and dose-dependent increase (↑↑) pf CZ-induced mortality, $ED_{50}$ (causing deaths in 50% of animals) being 0.15 (0.12–0.19) mmole/Kg

2-SLEEPING TIME FOLLOWING CDO-TREATMENT

In the untreated animals, CDO 100 mg/Kg i.p. induced sleep lasting 20-30 min. Sleeping time was defined as the time elapsing from the loss to the recovery of the righting reflex. Pretreated animals were observed up to a maximum of 6 h. Theophylline reduced (↓ ↓) CDO-induced sleeping time in a dose-dependent manner and the dose producing 50% decrease of the control value was 0.075 (0.046-0.121) mmole/kg. The results of both tests are shown in table 2 as: 0=no effects in comparison to the control values (↑) or (↓)=increase or decrease in comparison to the control

What is claimed is:

1. A compound having antiasthmatic activity characterized by the formula

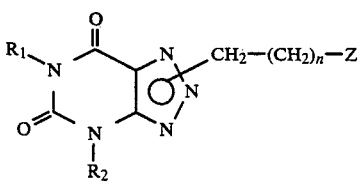
(II)

wherein:
R₁ is a hydrogen or a lower alkyl of from one to six carbon atoms or a phenylmethyl group
R₂ is a lower alkyl of from one to six carbon atoms or a phenyl or a phenylmethyl group
n=from 1 to 3

wherein:
R₃ and R₄ are lower alkyl of one to four carbon atoms or together represent either a saturated aliphatic hydrocarbon chain which with the nitrogen atom forms a five or six member ring or a saturated aliphatic hydrocarbon chain interrupted with oxygen as a heteroatom which with the nitrogen atom forms a five or six member ring; and wherein the substitution in the triazole ring concerns the 7- or 8- or 9-position, or a physiologically acceptable salt thereof.

2. A pharmaceutical composition suitable for oral, rectal, parenteral, inhalant administration and/or topical use, useful in the treatment of asthmatic diseases, devoid of significant side effects both on the central nervous system and on the cardiocirculatory system and which contains an effective amount of a compound of claim 1 or a physiologically acceptable salt thereof in association with normal pharmaceutical excipients.

3. 8-azaxanthine compound according to claim 1 which is 3-(2-methyl-butyl)-7-(2-diethylaminoethyl)-8-azaxanthine.

4. 8-azaxanthine compound according to claim 1 which is 3-(2-methyl-butyl)-8-(2-diethylaminoethyl)-8-azaxanthine.

5. 8-azaxanthine compound according to claim 1 which is 1-n-propyl-3-phenyl-7-(2-diethylaminoethyl)-8-azaxanthine.

6. 8-azaxanthine compound according to claim 1 which is 1-n-propyl-3-phenyl-8-(2-diethylaminoethyl)-8-azaxanthine.

7. 8-azaxanthine compound according to claim 1 which is 1-n-propyl-3-phenyl-9-(2-diethylaminoethyl)-8-azaxanthine.

8. 8-azaxanthine compound according to claim 1 which is 1-n-propyl-3-(2-methylbutyl)-7-(dimethylaminoethyl)-8-azaxanthine.

9. 8-azaxanthine compound according to claim 1 which is 1-n-propyl-3-(2-methylbutyl)-8-(dimethylaminoethyl)-8-azaxanthine.

10. 8-azaxanthine compound according to claim 1 which is 1-n-propyl-3-phenyl-7-(2-morpholino-ethyl)-8-azaxanthine.

11. 8-azaxanthine compound according to claim 1 which is 1-n-propyl-3-phenyl-8-(2-morpholino-ethyl)-8-azaxanthine.

12. 8-azaxanthine compound according to claim 1 which is 1-n-propyl-3-phenyl-9-(2-morpholino-ethyl)-8-azaxanthine.

13. 8-azaxanthine compound according to claim 1 which is 1-n-propyl-3-phenyl-7-(2-piperidinoethyl)-8-azaxanthine.

14. 8-azaxanthine compound according to claim 1 which is 1-n-propyl-3-phenyl-8-(2-piperidinoethyl)-8-azaxanthine.

* * * * *